United States Patent
dela Houssaye (10) Patent No.: US 7,618,372 B2
(45) Date of Patent: Nov. 17, 2009

(54) LASER GUIDED EYE MEASURING DEVICE AND METHOD FOR USING

(76) Inventor: Arthur Joseph dela Houssaye, 249 Corporate Dr., Houma, LA (US) 70360

( * ) Notice: Subject to any disclaimer, the term of this patent is extended or adjusted under 35 U.S.C. 154(b) by 796 days.

(21) Appl. No.: 10/710,348

(22) Filed: Jul. 2, 2004

(65) Prior Publication Data

US 2006/0025685 A1    Feb. 2, 2006

(51) Int. Cl.
*A61B 8/00* (2006.01)
*A61B 3/10* (2006.01)

(52) U.S. Cl. .................. 600/452; 600/449; 351/205

(58) Field of Classification Search ............... 600/427, 600/437, 438, 449, 452; 351/210–212, 200, 351/205

See application file for complete search history.

(56) References Cited

U.S. PATENT DOCUMENTS

| | | | | |
|---|---|---|---|---|
| 4,154,114 A | * | 5/1979 | Katz et al. | 73/629 |
| 4,237,901 A | * | 12/1980 | Taenzer | 600/443 |
| 4,764,006 A | * | 8/1988 | Hamano et al. | 351/211 |
| 4,848,340 A | * | 7/1989 | Bille et al. | 606/4 |
| 4,930,512 A | * | 6/1990 | Henriksen et al. | 600/452 |
| 5,056,522 A | * | 10/1991 | Matsumura et al. | 600/405 |
| 5,141,302 A | * | 8/1992 | Arai et al. | 351/205 |
| 5,369,454 A | * | 11/1994 | Reinstein et al. | 351/201 |
| 5,442,412 A | * | 8/1995 | Frey et al. | 351/223 |
| 5,776,068 A | * | 7/1998 | Silverman et al. | 600/443 |

* cited by examiner

*Primary Examiner*—Long V Le
*Assistant Examiner*—Jacqueline Cheng
(74) *Attorney, Agent, or Firm*—McGlinchey Stafford, PLLC (57) ABSTRACT

Laser guided fixation system and method for assuring alignment, constant pressure, and stationary positioning during ultrasound measurement of the eye: The invention employs a stable multi-purpose platform that carries a prior art ultrasonic probe used to measure the axial length of the eye, a projected laser spot as a fixation device, a gravity dependent swing arm with dual levels to maintain constant orientation and adequate pressure on the eye during measurement and a headpiece which keeps the entire apparatus stationary in relation to the patient's head. The method for using the invention describes a protocol which results in accurate and reproducible axial length measurements by establishing a means for assuring proper orientation, controlled pressure, and stationary positioning during axial length measurement of the eye.

10 Claims, 5 Drawing Sheets

LASER GUIDED EYE MEASURING DEVICE AND METHOD FOR USING

BACKGROUND OF THE INVENTION

The present invention relates to the measurement of intraocular distances using an ultrasonic probe, specifically for measuring the axial (anterior to posterior) length of the eye and particularly to using an ultrasound probe for accurately measuring the eye prior to lens calculation for cataract surgery.

The use of high frequency ultrasound to determine the anterior to posterior dimensions of the eye is well known. The measured axial length of the eye (distance from the cornea to the retina) is used to calculate the lens implant power to be used in cataract surgery. Although optical methods for measuring the axial length of the eye have been described, ultrasound measurement is the preferred method used by ophthalmologists. The technology and technique for making ultrasound measurements in ophthalmology are disclosed in Coleman, D., *Ultrasonography of the Eye and Orbit*. Lea & Febiger (1977). To make such measurements, a hand-held ultrasound probe is placed in contact with the cornea of the eye. The probe includes a transducer and a separate internal fixation light which the patient is instructed to view. As the patient views the internal fixation light, high frequency ultrasonic waves are reflected off of the back of eye, and these reflections are processed by the transducer and converted to quantifiable distances.

A description of the type of transducer used in this device can be found in U.S. Pat. No. 4,213,464 to Katz et al and a description of the complete measuring system can be found in U.S. Pat. No. 4,154,114 Katz et al Other U.S. patents which describe ocular measurement devices include U.S. Pat. No. 4,508,121 to Myers, U.S. Pat. No. 4,564,018 to Hutchinson et al and U.S. Pat. No. 4,576,176 to Myers.

Axial length measurement of the eye, although simple in concept is difficult in practice because the eye cannot be held stationary during the exam. Furthermore, the eye is pliable and excessive pressure applied to the eye during the measurement process will compress the eye and create inaccurate results. Finally, the measurement takes place on a human, which even when cooperative, typically has gross head, neck and body movement during the procedure.

Precise axial length measurement of the eye with ultrasound requires the following three components: 1) proper alignment of the ultrasound probe along the visual axis, 2) a mechanism of gently positioning the ultrasound probe against the eye during measurement with the correct and constant pressure applied to the eye by the ultrasound probe tip, and 3) stationary positioning of the ultrasound probe relative to the patient's head and eye during the measurement process.

Any one of these three variables, if not controlled, can confound the measurement process and introduce major errors during lens calculation for cataract surgery. Despite excellent technician skill, axial length measurement has been confounded by these variables since its inception. Numerous techniques have been developed in an attempt to minimize these sources of potential error.

A central problem discovered when utilizing and evaluating prior art for axial length ultrasound measurement is that each solution typically focuses on minimizing one or two potentially confounding factors, leaving the other variables to chance. The 3 main variables will be discussed in turn, the prior art solutions will be reviewed and discussed, and then the approach to solving all three of the potentially confounding variables to axial length measurement will be revealed.

1) Misalignment of the Probe during measurement: Misalignment of the probe during ultrasound measurement causes gross errors in axial length measurement as a result of off-center and/or off-axis positioning. Either of these errors will lead to incorrect calculations of the lens power used for cataract surgery. To minimize this problem, most current ultrasound probe tips have an internal fixation light provided by a fiber optic system to assist with fixation as described in U.S. Pat. No. 4,934,370 to Campbell. These internal fixation lights and the process of using them have limitations in their ability to assure proper alignment during ultrasound measurement. For example, the Sonomed A-Scan 5500 Ultrasound, a popular ophthalmic ultrasound measuring device, gives the following instructions for assuring proper alignment of the probe with the visual axis. "Instruct the patient to look towards the red fixation light in the probe tip and visually align the probe along the patient's visual axis". The fundamental limitation to this process is that the internal fixation point in the prior art is too large to adequately limit movement of the eye. As a result, patients cannot assist in maintaining axial alignment during measurement. Another fundamental problem is that the complex movements of the eye are extremely difficult to follow using a hand-held probe.

The first limitation of the internal fixation light provided in the prior art, U.S. Pat. No. 4,934,370 to Campbell, is the large size of the fixation light. In U.S. Pat. No. 4,934,370, pinhole optics are used to present a fixation target to the patient before and during contact of the probe with the eye to help maintain the patient's eye in alignment with the ultrasound waves emitted from the tip of the probe. This invention improves upon the previous process, where no fixation target was employed; however, the internal fixation system has limitations because of its large size. Campbell alludes to the large size of the fixation spot in his U.S. Pat. No. 4,934,370 in section 2 line 50 "as (the ultrasound probe tip) approaches, the point source increases in size. When the light source becomes SUFFICIENTLY LARGE, the fixation target becomes visible".

"Sufficiently large" refers to the size of the fixation target presented to the patient once the ultrasound probe of the prior art makes contact with the surface of the eye. Because of the inherent size of the pinhole optics and light scatter that occurs due to the tear film, the apparent size of a 1 mm fixation spot (a common size of pinhole used in pinhole optics) enlarges upon contact with the eye to subtend approximately 15 degrees in the central vision. Using the reduced schematic of the Gullstrand eye (American Academy of Ophthalmology Basic Science Book 3 Optics, 2002), it can be predicted that a 1 mm fixation spot in contact with the cornea is at least 8 times larger than the anatomical fixation capability of eye. A 1 mm fixation spot located at the cornea is sufficiently large to allow the patient to look approximately 15 Prism Diopters (7.5 degrees), in any direction and still have the "fixation target" overlying the central fixation point of the retina. Because of the large fixation spot, after the probe contacts the eye, the patient can have significant misalignment of the eye and still be looking at the large fixation point. Because of the large apparent size of a 1 mm fixation spot after it contacts the cornea, the current standard in the industry provides a rough guide for fixation, but does not precisely assure proper alignment of the ultrasound probe with the visual axis.

The alignment implications of having a large fixation spot is that the patient can maintain fixation of the large spot even when the tip of the probe is off center or the entire probe is misaligned and off the visual axis. The large spot size combined with the inherent difficulty of aligning the probe along the visual axis of a "live" eye leads to confounding errors during measurement. Visually aligning the probe along the visual axis while holding the probe stationary against the eye with the correct amount of pressure is quite difficult. Complex alignment relationships must be maintained between the probe and the eye at all times. All ultrasound probes have a tip and a tail. The tip emits the ultrasound signal and receives acoustic echoes from the internal ocular structures. The tail has a wire attached which is connected to the main computer. The tip-to-tail axis of the probe corresponds to the direction of the projected ultrasound beam emitted from the tip of the probe. For accurate results, precise alignment of both the tip and the tail of the probe must be maintained at all times. The two main categories of probe misalignment include "off center" problems, where the tip of the probe is not centered over the anatomical center of the cornea, and "off axis" problems, where the axis of the ultrasound probe does not correspond to the visual axis of the eye being measured. Either of these positioning errors will give inaccurate readings.

Off Center Problems: The first aspect of achieving the correct ultrasound probe alignment is locating and maintaining the correct contact point between the tip of the probe and the topographical center of the cornea. The desired axis for measuring the axial length of the eye is along the visual axis. This relationship is most accurately described by the axis of Fick. As described in the American Academy of Ophthalmology Basic Science series 2002, Book 6, 2002, the "Y" axis of Fick is a sagittal axis passing through the center of the cornea, pupil and out through the posterior of the eye. To correctly place the tip of the probe on the center of the cornea, it must come in contact with the cornea at a spot that corresponds to the center of the pupil. While performing an ultrasound, the technician is typically positioned to the patient's side looking at the pupil from an oblique angle. Extrapolating the pupil's center from this location can be quite difficult. Typically, the patient's eye is wandering about throughout the measurement process because the fixation spot inside the prior art probe is too large to confine the movement of the eye as stated above. Since the cornea is a sphere, any off-center positioning of the probe tip will give an erroneously short measurement. In fact, short measurements are the most commonly encountered error seen in ultrasound axial measurements, in part because of the difficultly of visually maintaining the proper orientation of the probe on the moving cornea.

Off Axis Problems: The second aspect of achieving the correct ultrasound probe alignment is maintaining the proper relationship between the tip and the tail of the ultrasound probe. Once the tip of the probe is successfully placed on the geographic center of the cornea, the tail of the probe must be aligned with the tip in a way that the direction of the beam emitted from the tip of the probe is precisely aligned with the visual axis of the eye. Patients typically do not give feedback during this procedure, so there is no objective way of knowing if the ultrasound probe is correctly aligned. The fixation spot in the prior art is quite large, as described above, and can be seen at almost any angle of incidence with regard to the tip-to-tail alignment of the probe. Therefore, proper axial alignment cannot be objectively confirmed.

Axial alignment of the ultrasound probe, also known as the tip to tail alignment, is quite complex as it relates to a moving eye. To understand why it is so difficult to maintain this alignment, one must understand the geometry of the eye itself. The central axis of rotation of the eye is located at the center of the eye, not the cornea. This means that during measurement of the eye, if the patient inadvertently looks left 1 mm, the cornea moves 1 mm to the left while the retina moves 1 mm to the right. In this situation, the technician performing the ultrasound would need to quickly move the tip of the probe 1 mm to the left along an imaginary spherical meridian, while moving the tail of the probe 3-4 mm to the left, depending on the length of the probe. This would need to be done rapidly but without changing the force applied to the cornea by the probe tip. This extremely complex movement is very difficult to perform in a "live" eye that has the ability to move at a much higher rate of speed than the hand that is trying to follow it. In addition to the fine movements of the eye, the patient's head is also unstable and tends to move during the procedure.

Finally, most patients tend to have an avoidance response and their entire body moves away from the technician during the course of the measuring process thereby altering critical landmarks and making it quite difficult to maintain proper alignment.

In summary, due to the large fixation spot size of the prior art, the patient can look 15 prism diopters (7.5 degrees) in any direction and still be looking directly at the fixation spot. The technician can move the probe "off center" in any direction and still have the fixation spot fully visible. The axial alignment of the probe (tip to tail alignment) can be significantly "off axis" yet the patient can still clearly see the fixation spot. Due to these limitations, the internal fixation spot presented in the prior art is not the ideal way to maintain fixation during axial length measurement of the eye with ultrasound. It is no surprise that difficulty abounds in attempting to provide consistently accurate ultrasound readings.

2) Excessive or inadequate force applied during measurement: Attempts have been made to dampen and modulate the pressure that is placed on the eye while taking axial length measurements with an ultrasound probe. One notable invention that attempts to accomplish this is the Hand-held Spring Loaded Probe, U.S. Pat. No. 4,930,512 to Henriksen et al The prior art focuses on applying constant pressure to the eye by way of a spring dampened hand-held probe that aids in avoiding compression of the eye by limiting the maximum force applied during measurement.

This apparatus works relatively well in practice; however, there are two limitations to the proposed mechanism.

The first limitation is that the device must be held in the technician's hand and the problems of "off-center" and "off-axis" alignment discussed above become a confounding problem. The device can be connected to a slit lamp for more precise control, but there is still no inherent way to assure alignment with the visual axis.

The second limitation is that the resistance applied by the spring to the tip of the probe is fixed at a certain amount. This means that if the intra-ocular pressure is less than this amount, the probe will compress the eye and cause short readings. This probe dampens excessive pressure in the plane directly to and away from the eye, but any tangential movement on the surface of the eye moves the inner barrel of the spring loaded probe against the side wall of the outer sleeve and may decrease the ease with which the two sleeves slide past one another causing the resistance applied to the tip of the device to increase, thereby compressing the cornea.

3) Stabilization of the probe during measurement: This problem has been addressed in prior art by two different approaches. The first approach involves mounting the ultrasound probe on a slit lamp and having the patient sit at the slit lamp during the measurement process. This approach increases stability, only to the extent that the patient remains in perfect alignment with the slit lamp. It does not address the compression of the cornea, nor does it address the axial alignment issue. The second approach involves using a water immersion bath which gives the probe some ability to move towards and away from the eye during the measurement without compressing the eye. This approach addresses the compression issue, since the intervening water bath prevents contact between the probe and the eye; however, it does not address the axial alignment issue. Furthermore, the water bath technique takes much longer to perform, involves laying the patient in a supine position, using a lid speculum and requires the use of a coupling agent (water bath) which can be messy. Due to limitations listed above, neither the slit lamp technique nor the water bath technique fully address all three limitations of ultrasound measurement of the eye, which include, 1) proper alignment of the ultrasound probe along the visual axis, 2) a mechanism of gently positioning the ultrasound probe against the eye during measurement with the correct and constant pressure applied to the eye by the ultrasound probe tip, and 3) stationary positioning of the ultrasound probe relative to the patient's head and eye during the measurement process.

SUMMARY OF THE INVENTION

The present invention relates to a device for biasing an ultrasound probe against a human eye for the purpose of obtaining the axial length of the eye to be used in intra ocular lens calculations for cataract surgery.

The invention consists of a prior art headpiece and a series of six joints and hinges which keep the entire apparatus stationary in relation to the patient's head. The invention employs a stable platform that carries a prior art ultrasonic probe used to measure the axial length of the eye. A projected laser spot acts as a fixation device and is uniquely coupled to the ultrasound probe in a way that assures perfect alignment with the visual axis. The device employs a gravity dependent swing arm with dual levels to maintain constant orientation and adequate pressure on the eye during measurement.

This invention uses a laser fixation spot presented to the fellow eye to accomplish accurate positioning of both eyes. Other prior art, U.S. Pat. No. 5,776,068 to Silverman et al has used the concept of a fixation light presented to the second eye to control the movement of the first eye, although not in the same way as this device. Silverman used an independently mounted fixation target in conjunction with a corneal ultrasound scanner. Silverman's system, method, and anatomical area of measurement are fundamentally different from this invention, but both Silverman and this concept employ a well known trait called ocular concurrence, also known as orthophoria.

Ocular concurrence is the normal default ocular alignment in which the central retina (fovea) of each eye is directed to the exact same point in space. The visual direction of the central retina (fovea) is termed the visual axis and normally with central fixation is located straight ahead. The subconscious process of aligning the axis of both eyes is necessary for binocular vision and allows both eyes to fixate and follow an object through space, such as a bird flying overhead.

If at any time, the eyes are not concurrently aligned, the person will typically report double vision. People who have normal ocular concurrence and whose eyes are inherently straight are said to be orthophoric. In the orthophoric person, there is concurrence of the visual axis of both eyes even when one eye is closed or obstructed. The principle of orthophoria is employed in this device to align the eyes for testing.

Specifically, by aligning one eye to a point source in a person with normal concurrence (orthophoria), then by definition the second eye is lined up with the first. In our device, the eye that is being measured is occluded by the ultrasound probe, while the other eye fixates on a target generated by a laser pointer device that is coupled in perfect alignment with the ultrasound probe. The laser device projects a ray of laser light precisely 180 degrees from the axis of the emitted ultrasound beam. By employing this unique coupling technique, the visual axis of the eye being measured is always perfectly aligned with the incident ultrasound beam assuming the patient is orthophoric and is fixating on the projected laser target. The distance at which the projected laser target is presented to the eye does not impact the accuracy of the process due to the inherent synkinesis of the accommodative convergence response of the eye. Specifically, the eyes automatically converge when the fixation target is presented more closely and they automatically diverge to become parallel as the target moves toward infinity. This inherent principle of ocular alignment allows the technician to place the laser target grid at various distances while still preserving the integrity of measurements with this invention.

In contrast to the large fixation spot used in the prior art, our device presents a pin point spot on any wall 10 feet away that subtends about one minute of arc in the visual axis (There are 60 minutes of arc in each degree). By comparing the apparent size of the "pinhole optics" fixation point from the prior art and our device, it can be said that the prior art has a fixation "spot" that appears 900 times larger than the fixation spot in this invention. The fixation target of the prior art is displayed immediately prior to axial length measurement, but blurs and enlarges during measurement. In contrast, the fixation target in the invention is displayed prior to and throughout the measurement process. The more precise fixation point in the invention appears extremely small and thus allows the eye to remain completely stationary during the ultrasound measurement procedure.

Viewing a 1.0 mm fixation spot at 10 ft is a very precise way to orient the eye and maintains both eyes in a completely stationary state during the entire ultrasound exam. Viewing a 1.0 mm fixation spot located at the surface of the cornea, as used in the prior art, gives the fixation spot an apparent size that is 900 times larger than the fixation spot used in the invention.

Due to the small fixation point of the invention and the principle of orthophoria, which is exploited to align both eyes during measurement, the invention allows perfect alignment between the interrogating beam of the ultrasound and the eye being measured at all times thus eliminating misalignment of the probe during measurement, which is the first of three potentially confounding variables.

The next design feature of the invention is the appropriate and constant application of pressure to the eye during ultrasound measurement. The pressure applied to the eye by the tip of the probe must be sufficient to keep the probe in contact with the eye yet not excessive which would compress the eye, thereby distorting the measurement.

Due to the inherent simplicity of our gravity dependent system and adjustable pressure application to the cornea, any variation in intra ocular pressure or corneal resilience can be addressed by following a two step protocol.

Step one is to assess the intra ocular pressure before starting the procedure. Once the intraocular pressure is noted, the amount of tension applied to the eye can be precisely adjusted as described below.

Step two involves closely observing the amount of indentation the probe creates on the eye as the procedure is being performed. This is accomplished by having the technician wear a head-mounted light that is directed at the contact point between the probe and the eye. A characteristic tear film meniscus or "ring of light" is visible around the edge of the probe when the correct pressure relationship exists between the probe and the eye. If too much or too little pressure is applied to the eye, the ring of light, (the tear film meniscus), becomes distorted alerting the technician to the problem. Too much pressure visibly compresses the eye and fundamentally changes the appearance of the tear film meniscus. The patient's head and the invention are adjusted until the appearance of the tear meniscus is correct. The amount of pressure applied to the probe tip against the eye is finely controlled by having the patient tilt their chin up or down. This is accomplished by using a grid on the wall at which the laser fixation point is directed. If the probe tip is indenting the eye, which indicates too much pressure, the patient is instructed to tilt their chin down and fixate the laser spot on a grid mark that is BELOW the previously assigned grid mark. Lowering the patient's chin changes the relationship of the swing arm to the gravitational pull of the earth decreasing the amount of pressure applied to the tip of the probe. Raising the patient's chin and the laser spot on the target grid increases the gravitational pull on the swing arm, thus increasing the pressure on probe tip as it contacts the eye.

The gravity dependent swing arm apparatus is a unique solution to the vexing problem of how to reproducibly apply appropriate and constant pressure to the eye during ultrasound measurement. Using this technique, the amount of pressure can be adjusted to precisely match the needs of each particular patient and each eye and therefore the problem of excessive or inadequate force applied during measurement is eliminated. This infinite adjustability is an advantage compared to the prior art (Spring Loaded Ultrasound Probe) which has a predetermined amount of force applied to the eye by the probe at all times.

Once the correct pressure has been determined by looking at the probe tip as it contacts the eye, a note is made as to which grid mark produced the ideal pressure. Assuming the intra ocular pressure of the fellow eye is similar to the first eye, this same grid mark is used as a target for the measurement of the second eye. By using this technique, constant pressure to the probe tip is assured between both eyes.

The last key feature of the design is the inherent ability of the probe to stay properly positioned in relation to the patient's head. Once the probe is positioned, it will hold this position in relation to the patient's head, even if the patient moves their head, neck or body. This unique feature is the result of the probe being attached to the patient's head as its foundation and gives the probe unmatched stability. This feature addresses the third potential confounding factor while measuring the eye which is the stabilization of the probe during measurement.

BRIEF DESCRIPTION OF THE DRAWINGS

Preferred embodiments of the invention are shown herein with references to the drawing Figures in which similar elements are labeled similarly and wherein.

DETAILED DESCRIPTION OF THE INVENTION

Figures 1, 1B:
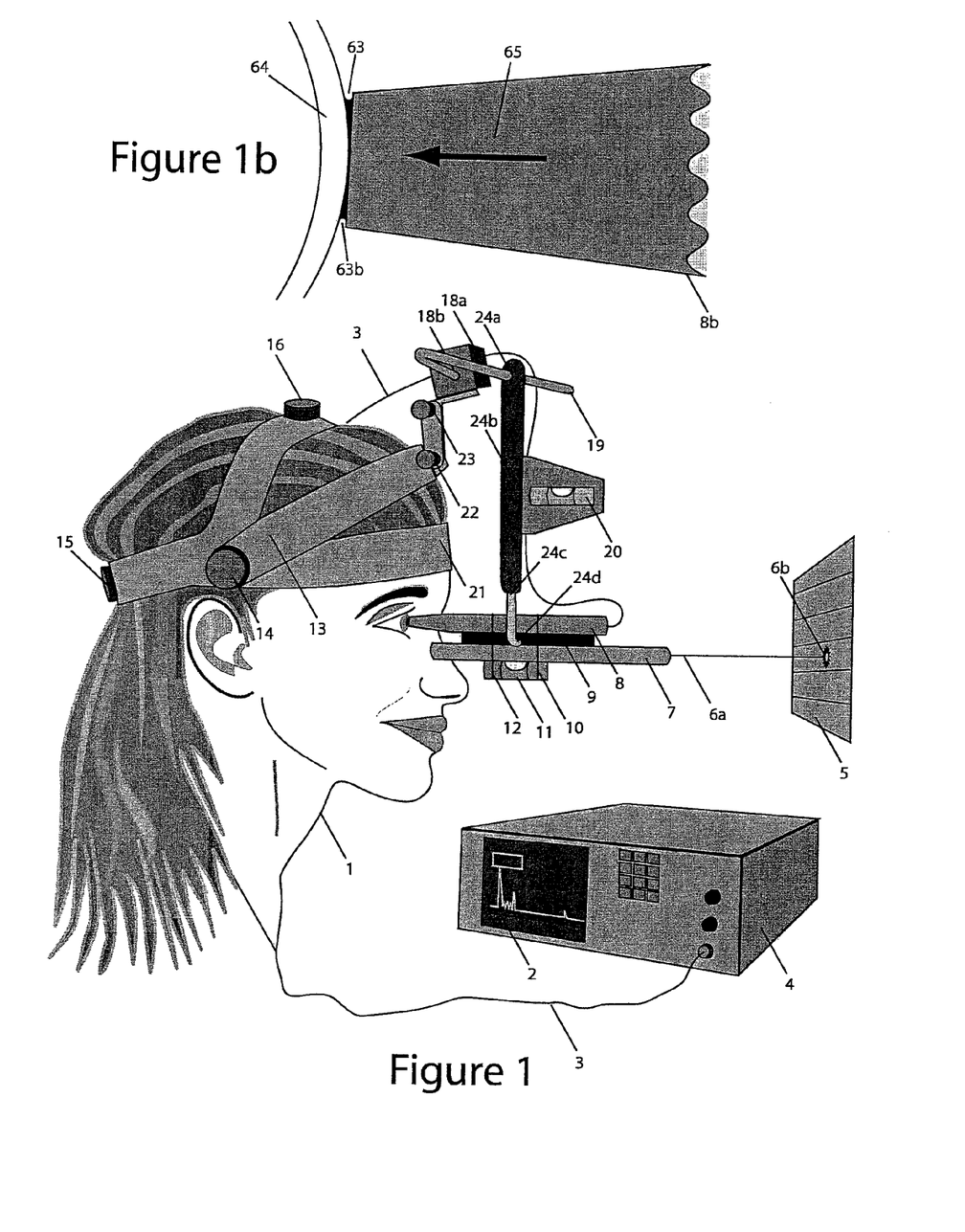
FIG. 1 is a side view of the entire apparatus in the correct measuring position.
FIG. 1b displays a magnified side view of the probe tip as it contacts the cornea with appropriate force thereby creating a correct tear meniscus.

Referring initially to FIG. 1, which is not necessarily drawn to scale, the illustration depicts a side view of a patient 1, the prior art ultrasound display screen 2, ultrasound probe wire 3, ultrasound computer 4, and ultrasound probe 8. The laser target grid 5 is located on the wall directly in front of the patient being measured. The laser projection device 7, emits an invisible laser beam 6a, which creates a laser point spot 6b, on the target grid. The carrying platform 9, is connected to the swing arm 24b, by way of a curved arm 24d. The laser projection device 7, ultrasound probe 8, and lower bubble level 11, are all attached to the carrying platform by way of retaining bands 10 and 12. The upper bubble level 20, is attached to the swing arm 24b at the midpoint of the swing arm. The swing arm is attached to the horizontal suspension bar 19. The articulation between the horizontal suspension bar and the swing arm is located at 24a.

The horizontal suspension bar articulates with the headpiece block 18a, at a rotational joint 18b. The headpiece block is rigidly attached to the headpiece arm 13 by way of two flexible joints numbered 22 and 23. The headpiece arm 13 is connected to the headpiece band 21 by way of a pivot joint 14. The front headpiece band 21 is maintained in tight apposition to the forehead by adjusting the tightness of the headband at the point 15 and 16, both of which are used to adjust the headpiece. The entire headpiece encompassing parts numbered 13, 14, 15, 16, 21, 22, 23 are considered prior art.

The carrying platform 9 is made from suitable wood that has a smooth channel on the top to hold the ultrasound probe 8. The wooden carrying platform has a smooth channel on the bottom to hold the laser pointer 7. Both channels are constructed to achieve a tongue in groove type fit between the carrying platform, the probe and laser. This fit is crucial to prevent any lateral movement of the probe or laser which ensures perfect alignment between the ultrasound and the laser pointer along the same axis. The carrying platform articulates with the lower end of the swing arm by way of a curved threaded metal rod 24d, which allows 360 degree rotation around the articulation joint 24d. This same threaded metal rod articulates with the lower end of the wooden swing arm 24c, and allows the carrying platform to rotate 360 degrees around the articulation joint 24c. These two joints allow the carrying platform to be positioned in any plane. The tenacious contact between the threads of the metal rod and the wood of the carrying platform and swing arm allows this device to remain stationary at all times unless actively repositioned, much like a "goose-neck" lamp. The invention can be adjusted to fit a range of different sized patients as the series of pivots labeled 14, 22, 23, 18b and 24a combine to give a range of motion of 12 inches in the vertical plane.

The wooden swing arm 24b is attached to the smooth brass horizontal swing arm suspension rod by a near frictionless rotational articulation 24a. The swing arm 24b, can rotate 270 degrees around this articulation 24a, and the swing arm can be moved laterally (left or right) to properly align the carrying platform in front of the left or right eye as needed for measurement. There are 8 inches of horizontal travel for the swing arm 24b, to move along the suspension bar 19, which allows measurement of any sized person. The articulation between the smooth brass horizontal suspension bar 19 and the wooden swing arm 24b is snug enough to prevent any rotational movement at this articulation, which maintains the ultrasound in its precise position during testing.

The smooth brass horizontal swing arm suspension rod 19, is bent at both ends to assume the configuration of a "D" with the round parts of the rod inserting in the headpiece block at point 18b. The articulation at 18b is extremely snug and the tenacious contact between the smooth brass rod and the wood headpiece block 18a, allows the horizontal suspension bar to remain stationary at all times, but to have the capability to rotate 270 degrees around the 18b articulation with manual repositioning.

The upper bubble level 20, moves only as a result of movement of the wooden swing arm around the 24a articulation. The lower bubble level moves in response to rotation of the carrying platform 9 around the 24d articulation and as a result of movement of the wooden swing arm around the 24a articulation.

The display screen 2 graphically displays reflected signals from the internal structures of the eye and also displays the calculated intra ocular lens power to be used during cataract surgery.

FIG. 1b displays a magnified view of the probe tip as it contacts the cornea 64. The close-up of the probe 8b is shown in gray tone. When in the correct position, the probe contacts the cornea with a force represented by the vector 65 that is sufficient to cause contact between the cornea and the probe, but not excessive enough to cause the cornea 64, to be compressed. The tear film meniscus formed between the cornea and the probe by the correct amount of force is shown by the concave upper meniscus 63, and the concave lower meniscus 63b. The technician watches the tear film meniscus and both bubble levels throughout the procedure to assure they maintain the correct configuration. The configuration of the device can be altered by having the patient move their chin up or down slightly by directing the patient to point the laser spot at a higher or lower line on the grid. The lines on the grid are labeled with numbers and colors to assist the patients with this task.

Figure 2:
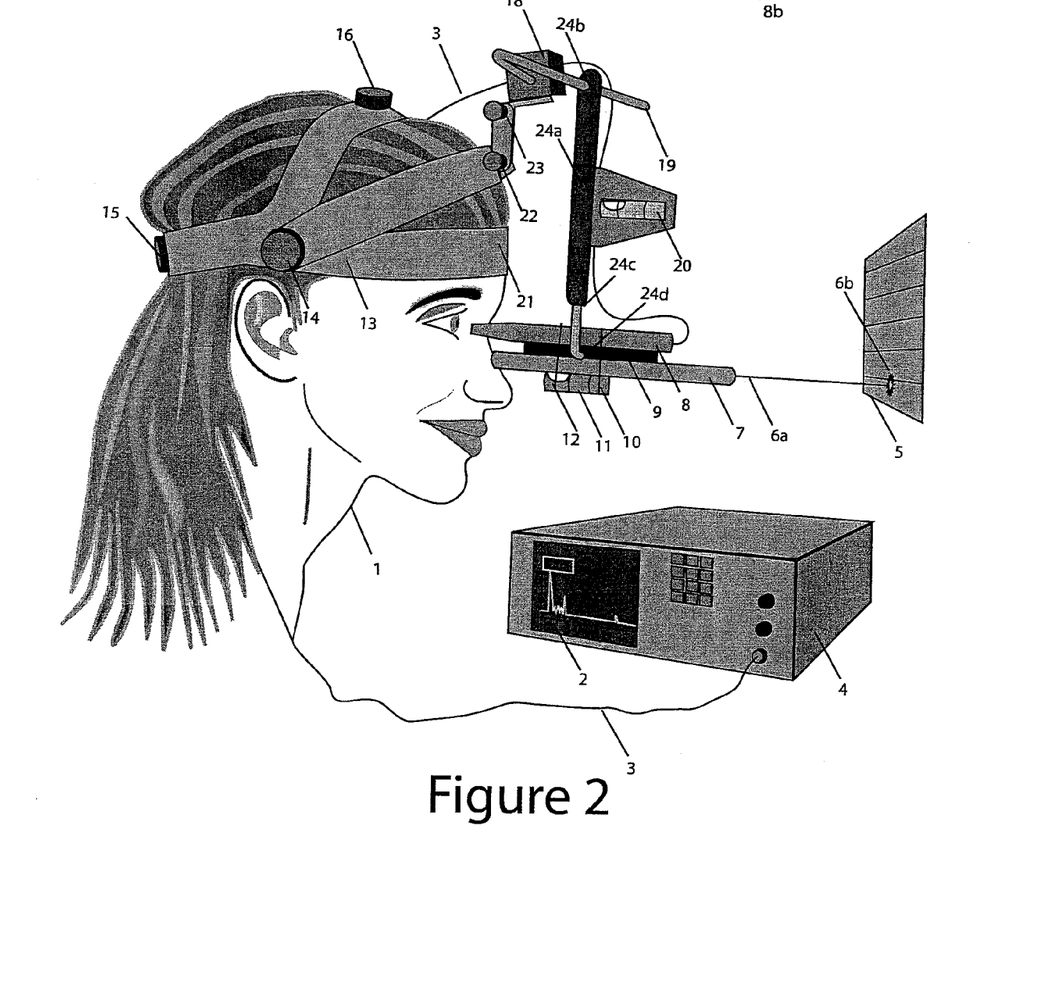
FIG. 2 is a side view of the entire apparatus demonstrating a "chin down" incorrect vertical positioning of the patient during the procedure.

FIG. 2 is a side view of a patient demonstrating incorrect "chin down" vertical positioning of the patient and invention during the procedure. Insufficient pressure to the probe tip can be noted during the measurement process by visualizing loss of contact of the probe tip with the eye. Also, note that the chin is lower than in FIG. 1. The projected laser point 6b is noted to be hitting the target grid 5 at a very low point on the grid and finally the upper bubble level 20 and the lower bubble level 11 show that the probe and the swing arm are incorrectly positioned as the bubble is located at the extreme end of the bubble level. Because of the numerous signs of incorrect positioning, it is easy to identify this type of malposition. To remedy this situation the patient is instructed to lift their chin to place the laser point 6b at the mid point of the target grid, as depicted in FIG. 1.

Figure 2B:
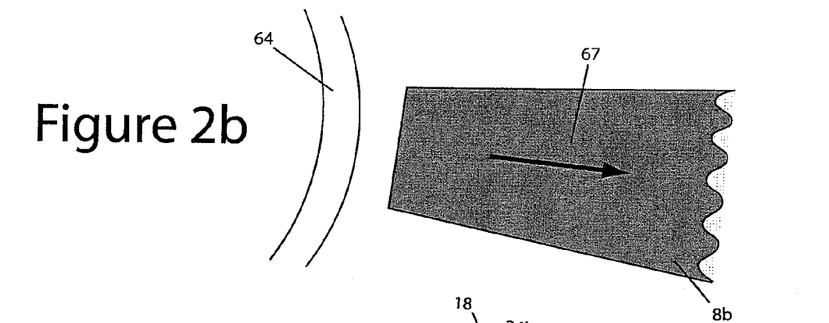
FIG. 2b displays a magnified side view of the probe tip as it loses contact with the cornea due to an incorrect "chin down" position of the patient during the procedure.

FIG. 2b displays a close-up of the probe tip 8b and the cornea 64 as and the force vector 67 that occurs when the patient's chin is too low. In this position, the probe tip loses contact with the cornea and therefore no measurements can be taken. For this reason, in addition to the visible space between the cornea and the probe and the abnormal bubble level position, this malposition is easy to recognize. To remedy this malposition, the technician asks the patient to lift their chin up slightly thereby elevating the laser spot 6b, to the proper position as shown in FIG. 1.

Figure 3:
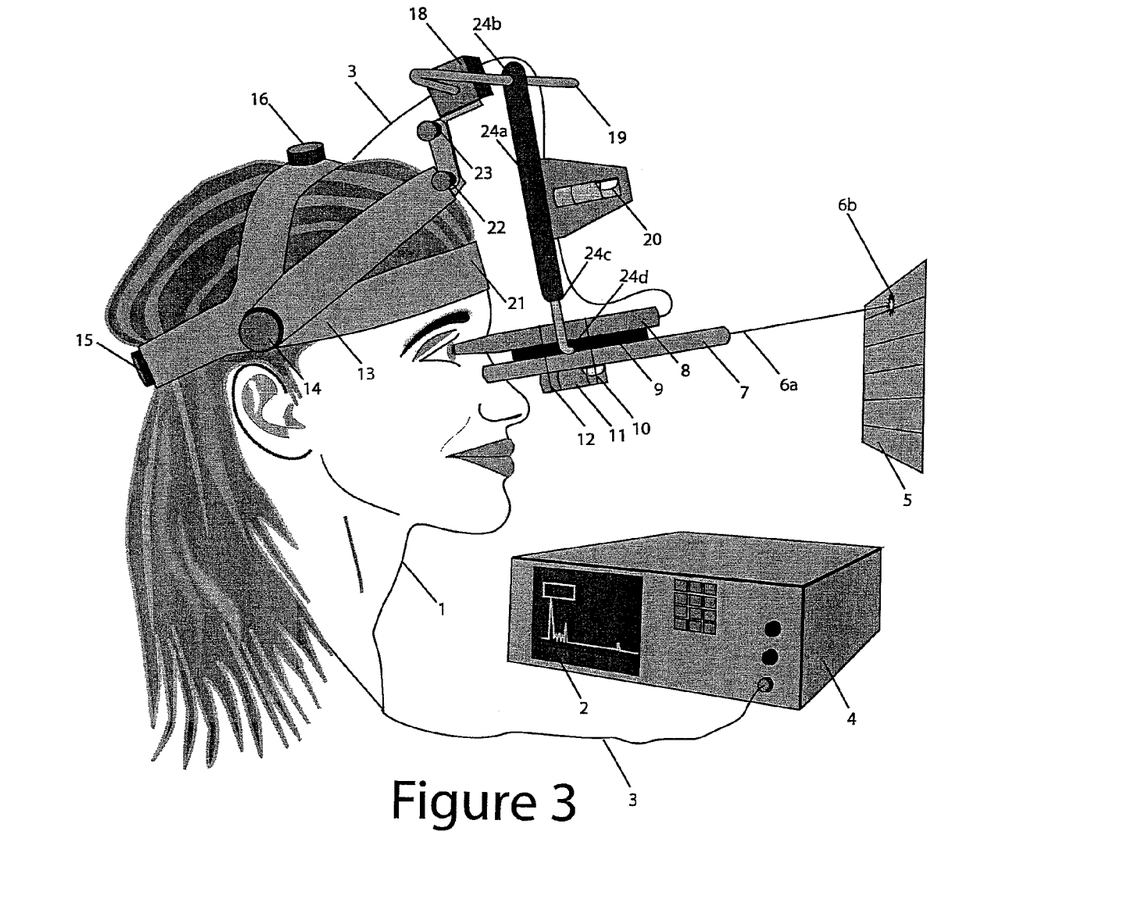
FIG. 3 is a side view of the entire apparatus demonstrating an incorrect "chin up" vertical positioning of the patient during the procedure.

FIG. 3 is a side view of a patient demonstrating "chin up" incorrect vertical positioning of the patient and invention during the procedure. Excessive pressure to the probe tip can be noted during the measurement process by visualizing compression of the cornea, an abnormal tear meniscus, abnormal position of the upper bubble level 20 and the lower bubble level 11, abnormally high position of the laser spot 6b on the laser target grid 5 and the elevation of the patient's chin. Because of the numerous signs of incorrect positioning, it is easy to identify this type of malposition. To remedy this situation the patient lowers their chin to place the laser point 6b, at the mid point of the target grid, as depicted in FIG. 1.

Figure 3B:
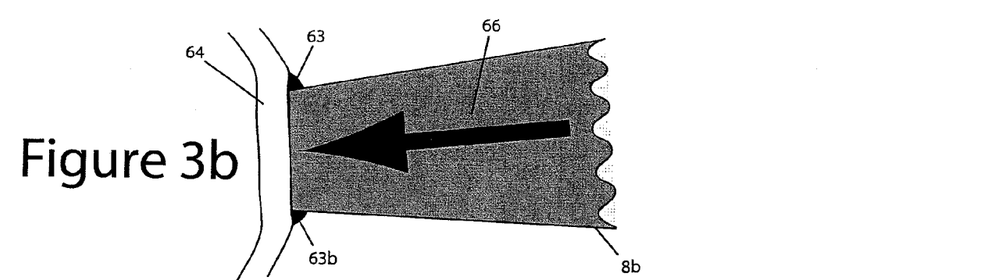
FIG. 3b displays a magnified side view of the probe tip with excessive force applied to the cornea resulting in compression of the cornea due to an incorrect "chin up" position of the patient during the procedure.

FIG. 3b displays a close-up of the probe tip 8b, the cornea 64 and the force vector 66 that occurs when the patient's chin is too high. In this position, the probe tip has excessive force and the cornea is compressed leading to incorrect and short measurements. The tear meniscus in this incorrect position is noted to be convex and located at the extreme edge of the probe tip and "spills over" the side of the probe 63 and 63b. To remedy this malposition, the patient is instructed to lower their chin slightly thereby lowering the laser spot 6b to the proper position as shown in FIG. 1.

Figure 4:
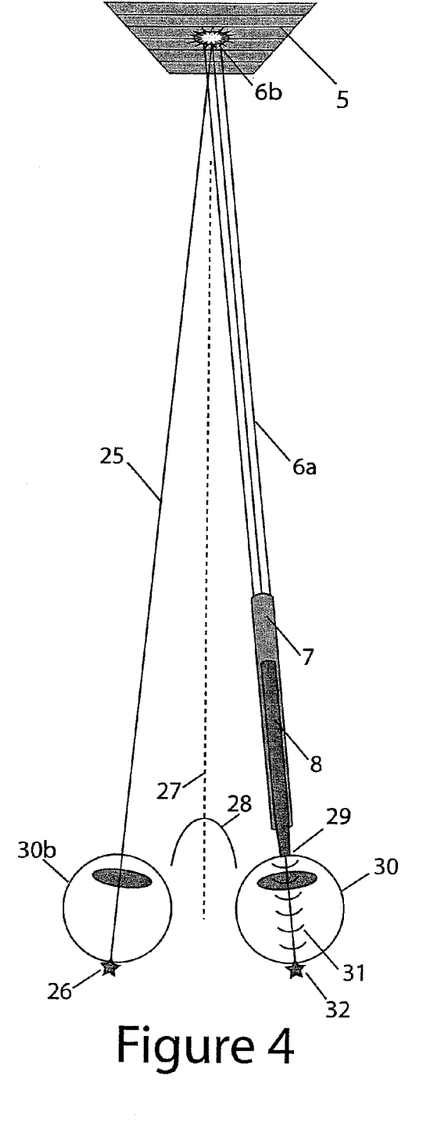
FIG. 4 is an axial plane view illustrating the correct horizontal alignment of the current invention with probe.

FIG. 4 shows the invention in an axial plane view looking down on the patient from above illustrating the correct horizontal alignment of the probe and the principles behind this alignment. In FIG. 4 the patient's face is oriented straight ahead, which is the desired position for the patient during ultrasound measurement. In this view the laser spot 6b is shown on the target grid 5 in the correct position. The patient's nose 28 is directed straight ahead at the target grid 5 as depicted by the dotted directional line 27. The eye being measured 30 is seen to be correctly aligned with the ultrasound probe 8. The probe 8 is contacting the eye at the apex of the cornea 29 and the emitted waves from the ultrasound probe 31 are directed at the fovea 32 of the eye being measured. As a result of the alignment between the ultrasound probe 8 and the laser pointer 7 the light projected out of the laser pointer 6a is perfectly aligned with the ultrasound pulses 31 emitted from the probe 8. The projected laser spot on the wall 6b, is observed by the fellow eye 30b and this eye, because of the principle of orthophoria as discussed above, precisely controls the direction of the contralateral eye 30. In the case of an orthophoric eye, both eyes will be directed at the laser spot 6b which is kept in perfect alignment with the ultrasound probe by the carrying platform (not shown). Due to this unique alignment principle, the eye being measured 30 is always in perfect alignment with the incident ultrasound waves 31 being emitted from the probe tip.

Figure 5:
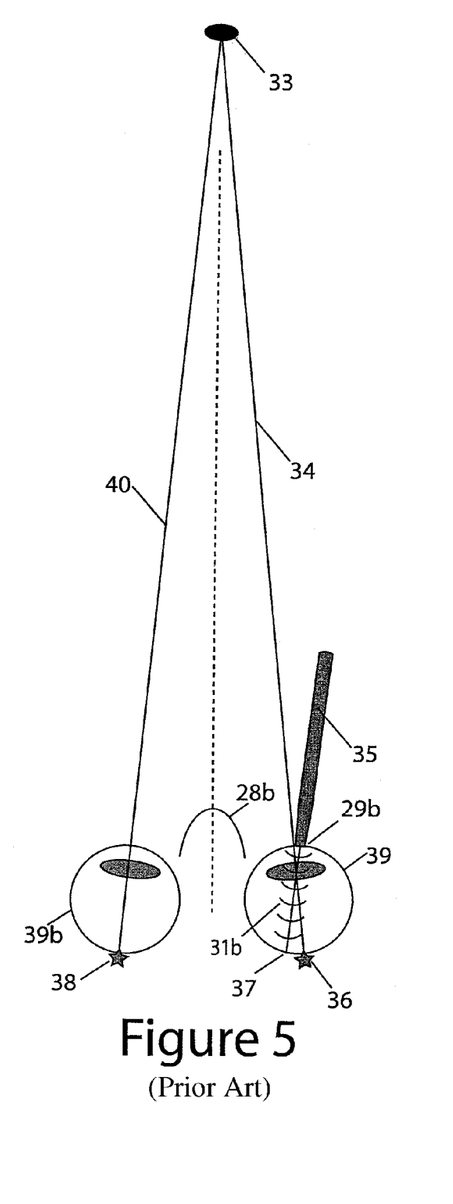
FIG. 5 is an axial plane view illustrating a commonly experienced misalignment problem that occurs in the prior art.

FIG. 5 shows prior art in an axial plane view looking down on the patient from above illustrating a commonly experienced misalignment problem that occurs in the prior art. Even with an internal fixation light in the ultrasound probe as described in the prior art above, precise fixation and confirmation of the visual axis is impossible because the internal fixation target becomes extremely large after the probe tip contacts the eye. During the measurement process, which takes a few minutes, the patient requires a visual target to anchor their eye and keep it from wandering. It is common, when using prior art devices, to have the patient look at some external object (like a spot on the wall) or fixation device that is independent of the probe to help keep both eyes from wandering during the procedure. In FIG. 5, the distance fixation point 33 is directly in front of the patient as can be noted by the orientation of the patient's nose 28b. The eye being measured 39 is seen to be correctly oriented towards the fixation point 33 as one would expect in an orthophoric patient; however, the probe is INCORRECTLY aligned with the visual axis of the eye. The probe 35 is contacting the eye lateral to the true apex of the cornea 29b and the emitted waves from the ultrasound probe 31b are intersecting the retina too far toward the nose 37 instead of the intended target of the fovea 36 in the eye being measured. As a result of the misalignment between the ultrasound probe 35 and the visual axis of the eye 34 these measurements will be incorrect. Because small errors in axial length translate into large errors in calculated lens power, errors of alignment such as these create major problems in determining lens power during cataract surgery. For example, an extremely small error in axial length measurement of 0.5 mm (about the thickness of 4 sheets of paper) will introduce a power calculation error of 1.25 diopters to the intraocular lens! The misalignment represented in FIG. 5 is common because it is very difficult to visually align the ultrasound probe with the patient's visual axis, especially when viewing the patient from the side (the typical situation during measurement). FIG. 5 illustrates the point that misalignment of the probe in the prior art can occur even when the patient directs their attention to a fixation spot on the wall.

Figure 6:
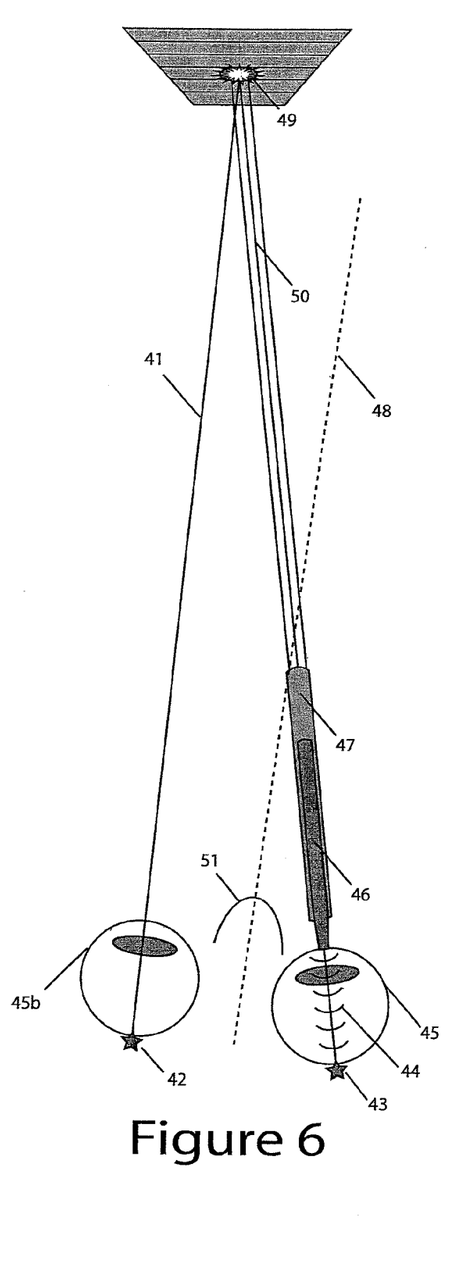
FIG. 6 is an axial plane view illustrating the correct horizontal alignment of the probe tip, even as the patient moves their head into an incorrect position during measurement.

FIG. 6 shows the invention in an axial plane view looking down on the patient from above illustrating the correct horizontal alignment of the probe tip, even as the patient moves their head into an incorrect position during measurement. In FIG. 6 the patient's face is oriented incorrectly to the right, which is NOT the desired position for the patient's head during ultrasound measurement. FIG. 6 illustrates the value of this invention's unique fixation device in patients even when they are being measured in an abnormal head position. Occasionally patients will turn their heads away from the desired measurement position during the measurement process. This typically occurs slowly during the measurement process and is so subtle that it may not be recognized by the technician. In FIG. 6, the laser spot 49 is shown on the target grid 5 in the correct position. The patient's nose 51 is directed to the right indicating incorrect head positioning as depicted by the dotted directional line 48 as sometimes occurs during measurement. Despite the misalignment of the head, the eye being measured 45 is seen to be correctly aligned with the ultrasound probe 46. The probe 46 is contacting the eye at the apex of the cornea, and the emitted waves 44 from the ultrasound probe 46 are directed at the fovea 43 of the eye being measured. As a result of the alignment between the ultrasound probe 46 and the laser pointer 47 the light projected out of the laser pointer 50 is coincident with the ultrasound pulses emitted from the probe 44. The projected laser spot on the wall 49 is observed by the fellow eye 45b and this eye, because of the orthophoria as discussed above, precisely controls the direction of the contralateral eye 45. In the case of an orthophoric patient, both eyes will be directed at the laser spot 49 which is kept in perfect alignment with the ultrasound probe by the carrying platform (not shown). Due to the unique alignment principle of this invention, the eye being measured 45 is always in perfect alignment with the incident ultrasound waves 44 from the probe tip, EVEN WHEN THE PATIENT'S HEAD IS INCORRECTLY POSITIONED.

Figure 7:
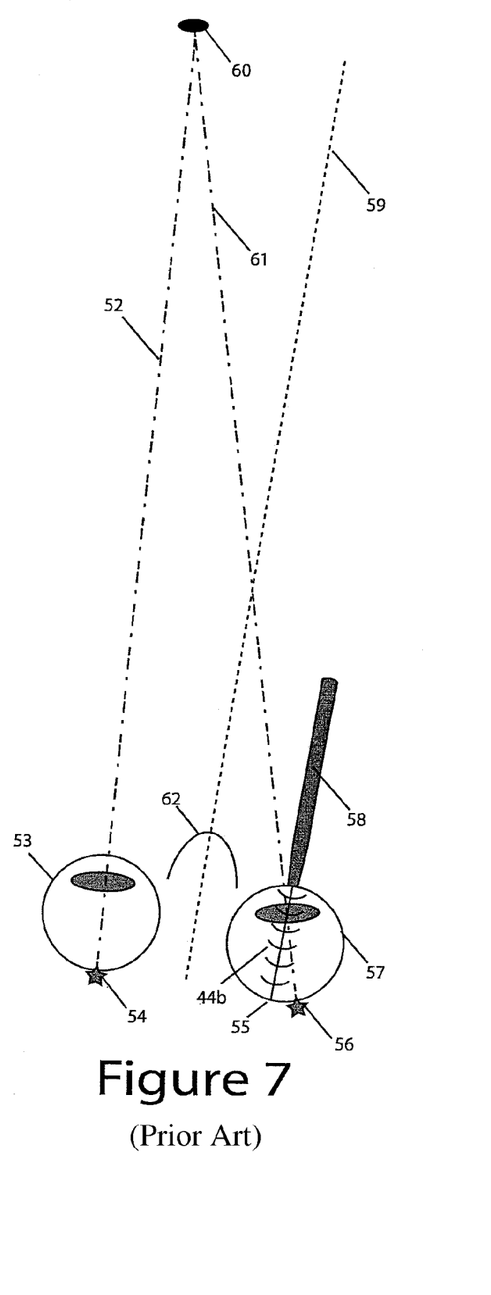
FIG. 7 is an axial plane view illustrating a commonly experienced misalignment problem that occurs in the prior art as a result of incorrect facial movement to the right.

FIG. 7 shows prior art in an axial plane view looking down on the patient from above illustrating a commonly experienced misalignment problem that occurs in the prior art. Even with an internal fixation light in the ultrasound probe as described in the prior art above, precise fixation and confirmation of the visual axis is impossible because the internal fixation target becomes extremely large after the probe tip contacts the eye. In FIG. 7 the patient's face is oriented incorrectly to the right, which is NOT the desired position for the patient's head during ultrasound measurement. Occasionally patients will turn their heads away from the desired measurement position during the measurement process. This typically occurs slowly during the measurement process and is so subtle that it may not be recognized by the technician. During the measurement process, which commonly takes a few minutes, the patient requires a visual target to anchor their eye and keep it from wandering, but even if the patient is fixated on the target, their head can sometimes turn away from the desired position during measurement. In FIG. 7, the distance fixation point 60 is directly in front of the patient, but the patient has inadvertently turned their head to the right, as can be noted by the orientation of the patient's nose 62 and the dotted line 59. The eye being measured 57 is seen to be correctly oriented towards the fixation point 60 as one would expect in an orthophoric patient; however, the probe is INCORRECTLY aligned with the visual axis of the eye. The probe 58 is contacting the eye lateral to the true apex of the cornea, and the emitted waves from the ultrasound probe 44b are intersecting the retina too far toward the nose 55 instead of the intended target of the fovea 56 in the eye being measured. As a result of the misalignment between the ultrasound probe 58 and the visual axis of the eye 61, these measurements will be incorrect. Small errors in axial length translate into large errors in calculated lens power. The misalignment represented in FIG. 7 is common because it is very difficult to visually align the ultrasound probe with the patient's visual axis, especially when the patient inadvertently rotates their face away from the desired measurement position. Taking alignment cues from the face will cause the probe to be aligned with the face 59 but misaligned with the desired visual axis 61. Viewing the patient from the side (the typical situation during measurement) makes this error more probable. FIG. 7 illustrates the point that misalignment of the probe in prior art can occur even when the patient directs their attention to a fixation spot on the wall as a result of inadvertent facial misalignment.

Method of Measurement: FIG. 1: First the patient is administered a topical anesthetic drop in both eyes. The ultrasound device 4 is turned on, calibrated, and the pertinent patient data entered into the device and displayed on the screen 2. The headpiece is placed on the patient's head and the headpiece is snuggly fit by turning headpiece knobs 15 and 16. The laser pointing system 7 is switched on. The patient is instructed to close both eyes. The ultrasound probe is manually positioned in front of the closed eye to be measured by grasping the carrying platform like a pen and moving it into the correct measuring position, which is directly in front of the eye with both bubble levels in the neutral position.

Once the apparatus is in position, the patient is instructed to open both eyes and look at the bright red laser spot on the target grid which is located on the wall directly in front of the seated patient at a distance of about 10 feet. The technician moves the patient's head and the carrying platform to position the laser spot on the middle grid line (even older and less cooperative patients can maintain this position with surprising ease). The patient is then instructed to keep the laser spot on the grid at the same point throughout the procedure by maintaining their position like a statue.

The probe is then brought into contact with the patient's eye in the desired position and the examiner releases the device which will maintain this position. The device maintains its position in space due to three key design attributes; 1) the inherent tension built into the joints and swivels in the apparatus, 2) the light weight of the swing arm and its appendages (seven ounces total) and 3) the neutral balance inherent in the carrying platform.

FIG. 1 is a side view of a patient that displays the correct vertical positioning for the laser during the procedure. The patient is sitting directly in front of the laser target grid 5 with the laser 7 pointed directly ahead so that the laser point strikes the laser target grid at mid point 6b. The upper bubble level 20 and the lower bubble level 11 are both in the neutral position with the bubble located directly in the middle of the level. The invention, once put into this configuration, will remain in this configuration without any additional support. The measurement procedure then involves simply activating the ultrasound with a foot pedal, and obtaining a series of measurements. There is no movement of the probe with relation to the patient's head or eye during the measurement process, and a low standard deviation between a series of measurements is quickly achieved.

When properly positioned, the gravity dependent swing arm keeps the probe tip gently positioned against the eye with constant pressure, yet does not apply so much pressure that the eye is compressed. It applies this pressure without the use of springs or pistons and is self supporting, leaving both hands of the technician free to stabilize the patient during the measurement process if necessary. The two bubble levels help to ensure that the swing arm 24b is in perfect position. The upper bubble level 20 determines the amount of pressure on the eye. To increase the pressure applied to the tip of the ultrasound probe, the patient is asked to move their chin up slightly. This upward movement is adjusted precisely by having the patient position the spot of the laser pointer on the target grid. Each line on the grid is labeled by a number and a color to assist with this process. By having the patient move their chin up and point the laser at a line higher on the chart, the pressure to the ultrasound probe is increased. If there is too much force applied to the probe tip, indentation of the cornea will occur, which can easily be observed by watching the contact zone between the probe tip and the cornea. If this occurs, the patient is instructed to point the laser spot at a lower position on the grid. Having the patient move their chin down to point the laser spot at a line lower on the grid decreases the pressure applied to the ultrasound probe tip. The correct measuring position occurs when both bubble levels are perfectly centered indicating neutral pressure on the eye.

Once the probe is in place, it is stationary. If the patient moves their head in any direction, the probe moves with the patient and there is no fluctuation of pressure on the eye or manual interference with the probe tip, therefore, the patient has no stimulus to blink. Because of this stability and constant pressure, there is no need for a wire speculum while performing the procedure. Once the probe is in position on the patient's eye, the patient is able to keep the eye open with no discomfort. This makes performing this procedure much faster compared to prior art procedures which occasionally require the use of a wire speculum to keep the eye opened.

Once the first eye has been measured successfully, the swing arm (24b) is moved laterally in front of the other eye. Using the same grid mark as a reference, the same process is repeated for the second eye. The entire measuring process takes only 2-4 minutes to perform. The rapid and accurate acquisition of measurements is a factor that makes this instrument appealing.

The invention claimed is:

1. An apparatus for measuring the axial length of an eye of a patient comprising:
   a laser which projects a laser beam along a laser beam axis;
   an ultrasound measuring device comprising a probe and a piezoelectric device for generating ultrasound for interrogating the dimensions of the eye and a computer for processing the interrogated dimensions, the probe being configured for directing focused ultrasound waves of the ultrasound measuring device along the visual axis into the eye,
   means for stabilizing the ultrasound measuring device in relation to the patient,
   means for mounting the laser and the ultrasound probe so that the projected laser beam axis is substantially coaxial with the interrogating axis of said ultrasound measuring device and the laser projects a fixation target while the eye is being interrogated, and
   means for assuring correct pressure applied to the ultrasound probe as it contacts the eye.

2. The apparatus of claim 1 wherein the means for stabilizing the ultrasound measuring device in relation to the patient comprises a standard headpiece to which attaches a carrying platform which stabilizes the probe with respect to the patient's head and eye.

3. The apparatus of claim 2 further comprising (i) the carrying platform attached to a swing arm that carries the ultrasound probe, and (ii) means for assuring the correct horizontal and vertical alignment of said ultrasound probe with relation to the gravitational field of the earth.

4. The apparatus of claim 3, wherein the means for assuring the correct horizontal and vertical alignment of said ultrasound probe with relation to the gravitational field of the earth comprises a bubble level.

5. The apparatus of claim 1 wherein the fixation target is a laser spot projected onto a grid.

6. The apparatus of claim 1 wherein the means for assuring correct pressure applied to the ultrasound probe as it contacts the eye comprises independently moveable joints designed to bring the ultrasound measuring device into direct contact with the eye and maintain a stationary relationship without additional manual assistance.

7. The apparatus of claim 1 wherein the means for assuring correct pressure applied to the ultrasound probe as it contacts the eye comprises a gravity dependent swing arm that applies a constant and adjustable force to the eye throughout the ultrasound measuring process.

8. The apparatus of claim 7 further comprising means for assuring the correct horizontal and vertical alignment of said ultrasound probe with relation to the gravitational field of the earth.

9. The apparatus of claim 8, wherein the means for assuring the correct horizontal and vertical alignment of said ultrasound probe with relation to the gravitational field of the earth comprises a bubble level.

10. A process of measuring the axial length of a patient's eye including the steps of: (a) administering one or more anesthetic drops; (b) fitting a headpiece on the patient; (c) aligning an ultrasound probe tip over the eye to be measured while reflecting a laser beam on a visual reference in the patient field of vision, the laser beam axis being substantially coaxial with an interrogating axis of ultrasound waves emitting from the ultrasound probe; (d) as needed, modifying the position of a swing arm to assure proper pressure is applied by the ultrasound probe tip during measurement; (e) as needed, modifying the position of a carrying platform to assure proper horizontal and vertical alignment of the interrogating axis from the ultrasound probe tip during measurement; (f) confirming by direct observation of the contact point between the ultrasound probe and the cornea that the correct pressure is being applied to the cornea during measurement; and (g) measuring the axial length of said eye with ultrasound upon contact with the eye.

* * * * *